(12) United States Patent
Sheth

(10) Patent No.: US 9,694,110 B2
(45) Date of Patent: Jul. 4, 2017

(54) BIODISINTEGRABLE MEDICAL DEVICES

(71) Applicant: Boston Scientific Scimed, Inc., Maple Grove, MN (US)

(72) Inventor: Piyush Sheth, Temecula, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 475 days.

(21) Appl. No.: 14/063,384

(22) Filed: Oct. 25, 2013

(65) Prior Publication Data

US 2014/0080921 A1     Mar. 20, 2014

Related U.S. Application Data

(60) Division of application No. 13/546,290, filed on Jul. 11, 2012, now abandoned, which is a continuation of application No. 12/327,905, filed on Dec. 4, 2008, now Pat. No. 8,241,657.

(60) Provisional application No. 61/005,287, filed on Dec. 4, 2007.

(51) Int. Cl.
| | |
|---|---|
| A61F 2/00 | (2006.01) |
| A61L 27/58 | (2006.01) |
| A61L 31/04 | (2006.01) |
| A61L 31/14 | (2006.01) |
| A61K 47/30 | (2006.01) |
| A61F 2/04 | (2013.01) |
| A61F 2/94 | (2013.01) |
| A61M 27/00 | (2006.01) |

(52) U.S. Cl.
CPC .............. *A61L 27/58* (2013.01); *A61K 47/30* (2013.01); *A61L 31/041* (2013.01); *A61L 31/042* (2013.01); *A61L 31/148* (2013.01); *A61M 27/008* (2013.01); *A61F 2/04* (2013.01); *A61F 2/94* (2013.01); *A61M 27/002* (2013.01)

(58) Field of Classification Search
CPC .......... A61L 27/58; A61L 31/41; A61L 31/42; A61L 31/148; A61F 2/04; A61F 2/94; A61M 27/02; A61M 27/08; A61K 47/30
See application file for complete search history.

(56) References Cited

U.S. PATENT DOCUMENTS

| | | | |
|---|---|---|---|
| 5,085,629 A | 2/1992 | Goldberg et al. | |
| 5,229,124 A | 7/1993 | Rei et al. | |
| 5,286,415 A | 2/1994 | Buckley et al. | |
| 5,414,079 A | 5/1995 | Banker et al. | |
| 5,531,716 A | 7/1996 | Luzio et al. | |
| 5,531,735 A | 7/1996 | Thompson | |
| 5,599,291 A | 2/1997 | Balbierz et al. | |
| 5,762,860 A | 6/1998 | Ashcroft | |
| 5,814,006 A * | 9/1998 | Planz | 604/8 |
| 6,072,100 A | 6/2000 | Mooney et al. | |
| 6,368,356 B1 | 4/2002 | Zhong et al. | |
| 6,608,014 B1 | 8/2003 | Schramm, Jr. et al. | |
| 6,627,749 B1 | 9/2003 | Kumar | |
| 6,627,750 B2 | 9/2003 | Wang | |
| 6,818,283 B2 | 11/2004 | Nakamura et al. | |
| 6,824,645 B2 | 11/2004 | Jaschinski | |
| 6,991,647 B2 | 1/2006 | Jadhav | |
| 8,241,657 B2 | 8/2012 | Sheth | |
| 2001/0033852 A1 | 10/2001 | Wang et al. | |
| 2002/0138154 A1 | 9/2002 | Li et al. | |
| 2003/0153983 A1 | 8/2003 | Miller et al. | |
| 2003/0199993 A1 | 10/2003 | Gellman et al. | |
| 2003/0224033 A1 | 12/2003 | Li et al. | |
| 2004/0022824 A1 | 2/2004 | Li et al. | |
| 2004/0147737 A1 | 7/2004 | Ecker et al. | |
| 2004/0249441 A1 | 12/2004 | Miller et al. | |
| 2005/0238690 A1 | 10/2005 | Li et al. | |
| 2006/0264912 A1 | 11/2006 | McIntyre et al. | |
| 2008/0097349 A1 | 4/2008 | Dillinger | |

OTHER PUBLICATIONS

V. Kumar et al., "Oxidized Cellulose Esters: I. Preparation and Characterization of Oxidized Cellulose Acetates—a New Class of Biodegradable Polymers", J. Biomater Sci Polym Ed. 2002; 13(3):273-86.

Lihua Zhu et al., "Examination of Aqueous Oxidized Cellulose Dispersions as a Potential Drug Carrier: I. Preparation and Characterization of Oxidized Cellulose-Phenylpropanolamine Complexes", AAPS PharmSciTech 2004 5 (4) Article 69, (http://www.aapspharmscitech.org) 1-7.

Lihua Zhu et al., "Examination of Aqueous Oxidized Cellulose Dispersions as a Potential Drug Carrier: II. In Vitro and In Vivo Evaluation of Phenylpropanolamine Release from Microparticles and Pellets", AAPS PharmSciTech 2004 5 (4) Article 70, (http://www.aapspharmscitech.org) 1-8.

"The Limited Oxidation of Cellulose with Nirotgen Dioxide in Carbon Tetrachloride", submitted by J.R. Parkinson for the degree of Doctor of Philosophy, Lawrence College, Appleton, Wisconsin, USA, Jun. 1957.

M. Fukuda, "Properties of Sustained Release Hot-Melt Extruded Tablets Containing Chitosan and Xanthan Gum", Int J Pharm. 310 (2006) 90-100.

"Thermoplastic Poly (Vinyl Alcohol) (PVOH)", Primary author: Nigel Hodgkinson and Michael Taylor, Source: Materials World, vol. 8, pp. 24-25, Apr. 2000, published at Azom.com.

* cited by examiner

*Primary Examiner* — David Browe

(57) ABSTRACT

The present disclosure relates to medical devices which contain one or more polymeric regions that are at least partially biodisintegrable in bodily fluid. These devices may be implanted or inserted into a subject for treatment of various diseases, disorders and conditions. The present disclosure further provides methods of slowing and/or accelerating the dissolution of such medical devices by administering a composition which alters the pH of the subject's urine.

18 Claims, 1 Drawing Sheet

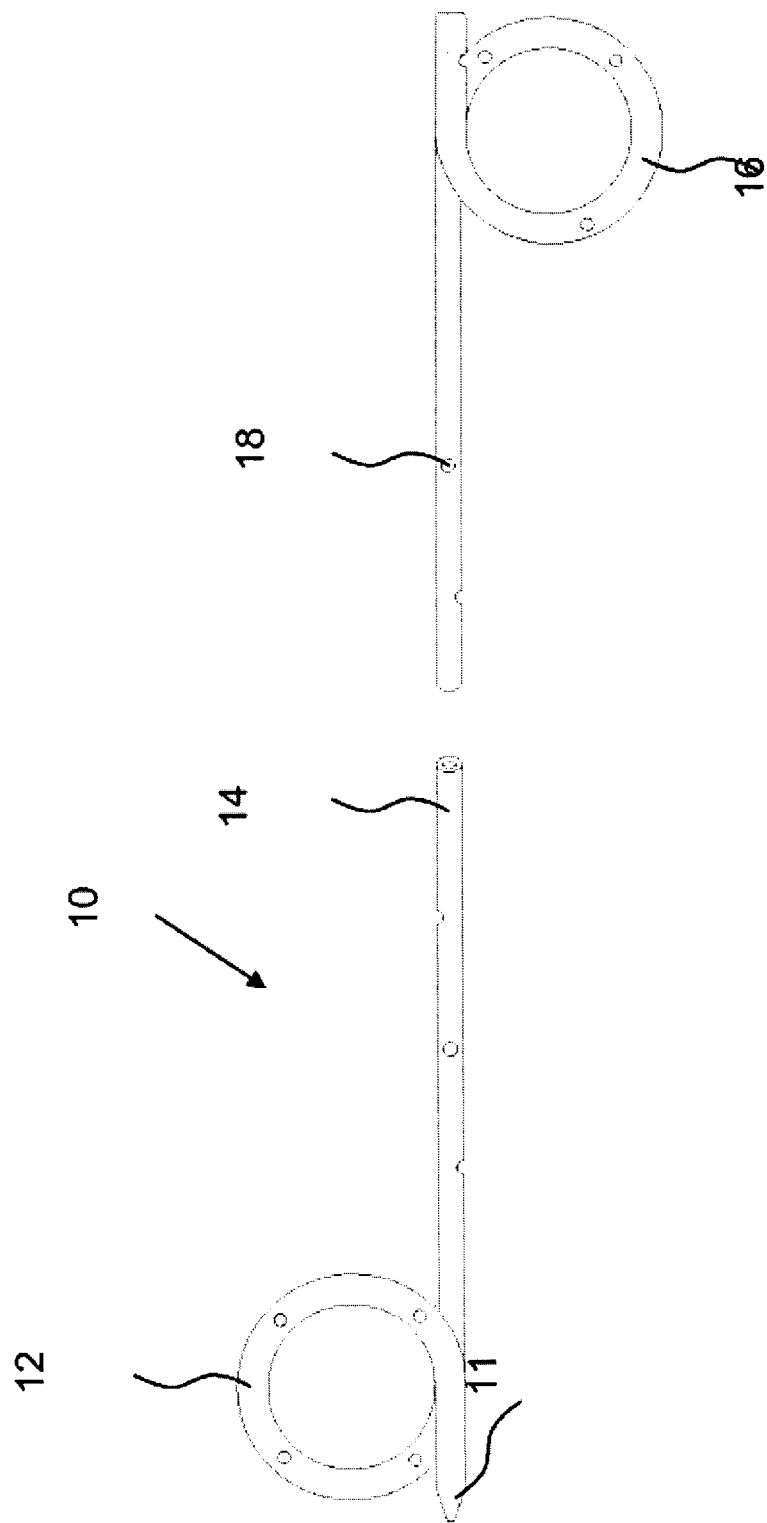

BIODISINTEGRABLE MEDICAL DEVICES

STATEMENT OF RELATED APPLICATIONS

This application is a divisional of U.S. patent application Ser. No. 13/546,290, filed Jul. 11, 2012, which is a continuation of U.S. patent application Ser. No. 12/327,905, filed Dec. 4, 2008, now U.S. Pat. No. 8,241,657, entitled "Biodisintegrable Medical Devices" which claims the benefit of U.S. Provisional Patent Application Ser. No. 61/005,287, filed Dec. 4, 2007, entitled "Biodisintegrable Medical Devices." Each of these applications is incorporated by reference herein in its entirety.

Field of the Invention

The present invention relates generally to medical devices, and more particularly to medical devices that contain one or more polymeric regions that are at least partially biodisintegrable in bodily fluid.

BACKGROUND OF THE INVENTION

Pain or irritation associated with medical devices of the urinary tract is a major concern in modern urology. As a specific example, kidney-ureter-bladder (KUB) devices such as ureteral stents are widely used to facilitate drainage in the upper urinary tract (e.g., from the kidney to the bladder).

For example, ureteral stents are used (a) in post-endourological procedures to act as a scaffold in the event of ureteral obstruction secondary to the procedure, (b) following procedures (e.g., ureteroscopies, endourerotomies, endopyelotomies, etc.) for the treatment of ureteral strictures and (c) in other instances where ureteral drainage may need to be facilitated, for example, due to the appearance of kidney stones, among other uses.

However, such stents are commonly associated with pain and discomfort in the bladder and/or flank area after insertion. There are various methods that have been employed to reduce the pain associated with such devices. For example, one way by which pain and discomfort may be minimized is to systemically administer pain-killing drugs to the patient. However, pain-killing drugs are associated with undesirable side effects, particularly with opioid analgesia which are commonly prescribed systemically for this purpose. Moreover, the subject is typically required to bear the pain, trauma and/or expense of going to a physician for stent removal.

SUMMARY OF THE INVENTION

According to an aspect of the present invention, the present invention provides medical devices which contain one or more polymeric regions that are at least partially biodisintegrable in bodily fluid. These devices may be implanted or inserted into a subject for treatment of various diseases, disorders and conditions.

An advantage of certain embodiments of the present invention is that medical devices may be provided which partially or completely disintegrate in bodily fluid, in some instances completely vanishing after the usefulness of the device has been served. For example, the devices may be disintegrated in some embodiments by urine that is voided out by a subject, by blood flow, and so forth. In the case of ureteral stents, for instance, such devices may be adapted to partially or completely disintegrate after their purpose of providing luminal scaffolding has been served. Pain and irritation associated with the presence of the device may decrease as the device disintegrates, eventually disappearing along with the device in some embodiments.

Another advantage of certain embodiments of the present invention is that medical devices may be provided which do not need to be removed from the body. For example, in the case of a completely biodisintegrable ureteral stent, the subject will avoid the pain, trauma and/or expense of going to a health care provider for stent removal.

These and other aspects, embodiments and advantages of the present invention will become immediately apparent to those of ordinary skill in the art upon review of the Detailed Description and any Claims to follow.

BRIEF DESCRIPTION OF THE DRAWING

The FIGURE is a side view of a ureteral stent, in accordance with an embodiment of the invention.

DETAILED DESCRIPTION OF THE INVENTION

A more complete understanding of the present invention is available by reference to the following detailed description of numerous aspects and embodiments of the invention. The detailed description of the invention which follows is intended to illustrate but not limit the invention.

In one aspect, the present invention provides medical devices which contain one or more polymeric regions that are at least partially biodisintegrable in bodily fluid. The devices may be implanted or inserted into a subject for treatment of various diseases, disorders and conditions.

As used herein, "treatment" refers to the prevention of a disease, disorder or condition, the reduction or elimination of symptoms associated with a disease, disorder or condition, or the substantial or complete elimination of a disease, disorder or condition.

Preferred subjects (also referred to as "patients") are vertebrate subjects, more preferably mammalian subjects and more preferably human subjects.

Examples of medical devices benefiting from the present invention include implantable or insertable medical devices, including those that are implanted or inserted to temporarily act as scaffolding for a body lumen, for example, ureteral stents, urethral stents, coronary vascular stents, peripheral vascular stents, cerebral stents, biliary stents, tracheal stents, gastrointestinal stents, and esophageal stents.

Particular medical devices benefiting from the present invention include kidney-ureter-bladder (KUB) devices such as ureteral stents. As noted above, these devices are used in post-endourological procedures to prevent ureteral obstruction secondary to the procedure, for example, (a) following various procedures for the treatment of ureteral strictures or (b) in other instances where drainage from the kidney to the bladder may need to be facilitated.

A schematic diagram of such one such stent 10 is illustrated in the FIGURE. The stent 10 is of a tubular construction and has a renal pigtail 12, a shaft 14 and a bladder pigtail 16. The pigtails 12, 16 serve to keep the stent 10 in place once positioned by the physician. The stent 10 is further provided with a tapered tip 11, to aid insertion, and multiple side ports 18 (one numbered) are arranged in a spiral pattern down the length of the stent body, which promote drainage. During placement, the ureteral stent 10 may be placed over a urology guidewire, through a cystoscope and advanced into position with a positioner. Once the proximal end of the stent is advanced into the kidney/renal calyx, the guidewire is removed, allowing the pigtails 12, 16 to form in the kidney and bladder. The stent shown is similar in appearance to the Percuflex® Ureteral Stent (Boston Scientific, Natick, Mass., USA). The Percuflex® Ureteral Stent, however, is formed from a biostable polymeric material (i.e., ethylene vinyl acetate copolymer), whereas the stent 10 is at least partially formed from a urine-disintegrable polymer.

For example, in some embodiments, the ureteral stent may comprise a first polymeric portion, which occupies the bladder and which is adapted to biodisintegrate in vivo. The first portion may comprise a biodisintegrable polymer. In these embodiments, the ureteral stent also comprises a second polymeric portion, which occupies the kidney and the ureter, and which biodisintegrates partially (e.g., because it is formed of a biodisintegratable polymer blended with a biostable polymer), biodisintegrates more slowly than the first portion, or does not biodisintegrate at all. The second portion may thus comprise a biodisintegrable polymer, a biostable polymer, or both. As indicated above, the bladder region is most commonly associated with patient pain or irritation after being deployed within a patient. Biodisintegration of the bladder-occupying portion, which may occur, for example, upon exposure to urine being voided by the patient, will be associated with improved patient comfort.

In some embodiments of the invention, ureteral stents are provided with a partially biodegradable region (e.g., the bladder portion, the entire device, etc.) which comprises a biodisintegrable polymer blended with a biostable polymer. Upon placement in a subject at least part of the biodisintegrable polymer is removed from the partially biodisintegrable region, thereby improving patient comfort.

A "polymeric" region is one that contains polymers, for example, from 50 wt % or less to 75 wt % to 90 wt % to 95 wt % to 97.5 wt % to 99 wt % or more polymers. Polymeric regions may correspond to an entire device or to a portion thereof.

By "biodisintegrable" polymer is meant that the polymer undergoes dissolution, degradation, resorption and/or some other in vivo disintegration process (biodisintegration process) over the time period for which the medical device is designed to reside in the body. Similarly, by "biostable" is meant that the polymer remains substantially intact over the time period for which the medical device is designed to reside in the body.

As used herein, "polymers" are molecules containing multiple copies (e.g., from 2 to 5 to 10 to 25 to 50 to 100 to 250 to 500 to 1000 or more copies) of one or more constitutional units, commonly referred to as monomers. As used herein, the term "monomers" may refer to free monomers and to those that are incorporated into polymers, with the distinction being clear from the context in which the term is used.

Polymers may take on a number of configurations, which may be selected, for example, from cyclic, linear and branched configurations. Branched configurations include star-shaped configurations (e.g., configurations in which three or more chains emanate from a single branch point), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers.

As used herein, "block copolymers" are copolymers that contain two or more polymer blocks that differ in composition, for instance, because a constitutional unit (i.e., monomer) is found in one polymer block that is not found in another polymer block. As used herein, a "polymer block" is a grouping of constitutional units (e.g., 5 to 10 to 25 to 50 to 100 to 250 to 500 to 1000 or more units). Blocks can be branched or unbranched. Blocks can contain a single type of constitutional unit (also referred to herein as "homopolymeric blocks") or multiple types of constitutional units (also referred to herein as "copolymeric blocks") which may be provided, for example, in a random, statistical, gradient, or periodic (e.g., alternating) distribution.

Examples of biostable and biodisintegrable polymers include a variety of homopolymers and copolymers and may be selected, for example, from one or more suitable members of the following: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, and polysaccharides, including fibrin, fibrinogen, collagen, elastin, chitosan, gelatin, starch, glycosaminoglycans such as hyaluronic acid; as well as further copolymers of the above.

In certain embodiments of the invention, medical devices are provided, part or all of which are soluble in aqueous solutions (e.g., at pH's encountered in the body of a subject, including neutral, mildly basic and mildly acidic pH's). As a result, part or all of such devices (e.g., an entire ureteral stent, only the distal bladder portion of a ureteral stent, the dissolvable portion of a blend of dissolvable and biostable polymers, etc.) may be become dissolved after implanting or inserting the device in a subject and upon exposure to bodily fluids. In these embodiments, the water soluble regions of the medical devices contain one or more dissolvable polymers.

Several water soluble polymers, many of which are also thermoplastic polymers, are described in U.S. Pat. No. 6,818,283, U.S. Pat. No. 6,072,100, U.S. Pat. No. 5,286,415, U.S. Pat. No. 5,229,124, U.S. Pat. No. 6,608,014 and U.S. Pat. App. Pub. No. 2001/0033852. These include, for example, polysaccharide homopolymers and copolymers, polyvinyl alcohol homopolymers and copolymers, polyethyloxyazoline homopolymers and copolymers, polyacrylamide homopolymers and copolymers, polyacrylic acid homopolymers and copolymers, polyvinyl pyrrolidone homopolymers and copolymers such as vinylpyrrolidone/vinyl acetate copolymers (e.g., Plasdone®, available from International Specialty Products, Wayne, N.J., USA) and styrene/vinylpyrrolidone copolymers, polyethylene oxide homopolymers and copolymers including POLYOX polymers produced by Union Carbide Corp., Bound Brook, N.J., USA, and melt processable poly(ethylene oxide) modified by grafting of polar vinyl monomers, such as poly(ethylene glycol)methacrylate and 2-hydroxyethyl methacrylate onto poly(ethylene oxide) as described in U.S. Pat. App. Pub. No. 2001/0033852.

Cellulose is a polysaccharide that is a linear polymer of glucose. It is quite plentiful, as it is the major structural constituent of plant cell walls. Various properties of cellulose, including its solubility in aqueous solutions among others, may be changed by adding entities to the cellulose that comprise functional groups such as ether, ester, hydroxyl, amino, and/or carboxylic acid (carboxyl) groups. These and otherwise modified polysaccharides based on cellulose are referred to herein as cellulose-derived carbohydrates.

Cellulose-derived carbohydrates that are soluble in aqueous solutions include hydroxyalkyl cellulose ethers and alkyl cellulose ethers such as hydroxypropyl cellulose ether and methyl cellulose ether products sold as METHOCEL from Dow Chemical, and thermoplastic, water-soluble cellulose derivatives such as those described in U.S. Pat. App. Pub. No. 2004/0147737.

Cellulose-derived carbohydrates that are soluble in aqueous solutions further include carboxylated celluloses. As used herein "carboxylated celluloses" are cellulose polymers (i.e., polyglucoses) that contain carboxyl functional groups, which are not ordinarily found in cellulose, and may contain other functional groups that are not ordinarily found in cellulose as well. Carboxylated celluloses include oxidized celluloses, carboxylated cellulose ethers (e.g., carboxymethylcellulose), carboxylated cellulose esters such as carboxyalkyl and carboxyaryl cellulose esters (e.g., cellulose monoesters of maleic acid, succinic acid, or phthalic acid), and oxidized cellulose alkylates (e.g., oxidized cellulose acetate), among others.

Carboxylated celluloses can be made through various processes including oxidation of cellulose and cellulose alkylates, etherification of cellulose, and/or esterification of cellulose, among other techniques.

The predominant reaction of oxidants (e.g., nitrogen dioxide, etc.) with cellulose is reportedly the oxidation to carboxyl groups of the primary hydroxyl groups that are found on the 6-carbon position of the glucose monomers in the cellulose. For this reason, oxidized cellulose is sometimes referred to as 6-carboxycellulose, although carbon atoms other than the 6-carbon may be oxidized. In addition to nitrogen dioxide (dinitrogen tetroxide), further oxidants that have been reported for the oxidation of cellulose include hypohalites, chlorine dioxide, permanganates, peroxides, dichromate-sulfuric acid, hypochlorous acid, gaseous chlorine, peracetic acid, periodic acid, persulfates, chromic acid, and hypochlorous acid. In addition to carboxyl groups and any unreacted hydroxyl groups, such oxidized celluloses may also contain aldehyde, ketone and/or other functionalities, depending on the nature of the oxidant and the reaction conditions used in their preparation. Some of these processes tend to preserve the cellulose in the form of fibers whereas other processes tend to break down the cellulose into particles of lower aspect ratio.

The carboxyl content of oxidized cellulose can range from less than 1 wt % to 5 wt % to 10 wt % to 15 wt % to 20 wt % up to the theoretical maximum of 25.6 wt % where all primary hydroxyl groups in the cellulose have been oxidized to carboxyl groups, although carboxyl contents of greater than 25.6 wt % can also be achieved by oxidizing other locations on the glucose units. Oxidized cellulose has been described as a weak polyacid with a reported pKa of about 3.6-4.0. It is typically insoluble in water but is soluble in mildly alkaline solutions.

U.S. Pat. No. 6,627,749 describes one particular method of preparing oxidized cellulose with different levels of oxidation and in high yields. The method involves treatment of a cellulose source with a mixture of phosphoric acid, nitric acid, and sodium nitrite at room temperature for a period until the desired level of oxidation (up to 25.6%) is achieved. According to this reference, oxidized cellulose with less than 3% carboxylic content serves as a non-degradable drug carrier, whereas oxidized cellulose containing equal to or greater than 3% carboxylic groups is useful as a biodegradable drug carrier.

Other methods of forming carboxylated cellulose involve etherification and esterification of cellulose. Etherification of cellulose by monochloroacetic acid yields carboxylated cellulose (i.e., carboxyalkyl cellulose, specifically, carboxymethyl cellulose) with relatively high carboxyl content, and the carboxylated cellulose products produced in this fashion are typically particles, rather than fibers, if the degree of substitution (DS) of carboxyl group is higher than 0.3. For further information, see, e.g., U.S. Pat. No. 6,627,750.

Esterification of cellulose may proceed, for example, by reaction with dicarboxylic acid anhydrides or chlorides, such as succinic anhydride, maleic anhydride, phthalic anhydride, or oxalyl chloride. For example, in U.S. Pat. No. 4,734,239, water-insoluble fibers of cellulose monoesters of maleic acid, succinic acid, or phthalic acid, which have a high absorption ability for water and physiological liquids, are produced by reacting a solution of activated cellulose and LiCl with a corresponding carboxylic acid anhydride in the presence of an esterification catalyst. The resulting carboxylated cellulose solution is wet spun into a coagulation agent.

Other processes involve a combination of the above processes. As an example, V. Kumar et al., "Oxidized cellulose esters: I. Preparation and characterization of oxidized cellulose acetates—a new class of biodegradable polymers," *J Biomater Sci Polym Ed.* 2002; 13(3):273-86 report oxidized cellulose acetates, with a carboxylic acid group contents of 20 wt %. These are reportedly created by the reaction of oxidized cellulose having 20 wt % carboxyl content with a mixture of acetic acid and acetic anhydride in the presence of sulfuric acid as a catalyst. The apparent pKa of the oxidized cellulose acetate is 3.7-3.9. The polymers are practically insoluble in water, but dissolve slowly at pH 7.4 in phosphate buffer solution.

Further information on carboxylated celluloses can be found in U.S. Pat. No. 6,627,750; U.S. Pat. No. 5,414,079; Lihua Zhu et al., "Examination of Aqueous Oxidized Cellulose Dispersions as a Potential Drug Carrier. I. Preparation and Characterization of Oxidized Cellulose-Phenylpropanolamine Complexes," *AAPS PharmSciTech* 2004 5 (4) Article 69; Lihua Zhu et al., "Examination of Aqueous Oxidized Cellulose Dispersions as a Potential Drug Carrier. II. In Vitro and In Vivo Evaluation of Phenylpropanolamine Release From Microparticles and Pellets," *AAPS PharmSciTech* 2004 5 (4) Article 70 (http://www.aapspharm-scitech.org); and the Introduction from a thesis entitled "The Limited Oxidation of Cellulose with Nitrogen Dioxide in Carbon Tetrachloride," submitted by J. R. Parkinson for the degree of Doctor of Philosophy, Lawrence College, Appleton, Wis., USA, June 1957.

Solubility of carboxylated celluloses may be increased, for example, by increasing the number of carboxyl groups, by neutralizing some or all of the carboxyl groups to form a carboxylated cellulose salt, or both. In this regard, the L. Zhu et al. articles above discuss the partial neutralization of oxidized cellulose using NaOH, with reported degrees of neutralization ranging from 0.2 or less to 0.5 or more (0.22 to 0.44 were preferred in those articles based on their ability to form aqueous dispersions for complexation with phenylpropanolamine-HCl).

In some embodiments, a soluble polymers such as carboxylated celluloses may be admixed with a biostable polymer. As noted in U.S. Pat. No. 6,627,750, the compatibility of cellulose with other polymeric materials may be improved when carboxylic acid groups are added to the cellulose.

Chitosan is a modified polysaccharide containing randomly distributed β-(1-4)-linked D-glucosamine and N-acetyl-D-glucosamine monomer units. Chitosan is produced commercially by the alkaline N-deacetylation of chitin, which is a cellulose-like polymer consisting primarily of unbranched chains of modified glucose, specifically N-acetyl-D-glucosamine. The degree of acetylation in commercial chitosans generally ranges from 60 to 70 to 80 to 90 to 100% although essentially any degree of acetylation is possible. Chitosan is also positively charged in acidic to neutral solutions with a charge density dependent on the pH and the degree of deacetylation. The pka value of chitosan generally ranges from 6.1 to 7.0, depending on the degree of deacetylation. Thus, while substantially insoluble in distilled water, chitosan is generally soluble in dilute aqueous acid (e.g., pH=6.5 or less). M. Fukuda, "Properties of sustained release hot-melt extruded tablets containing chitosan and xanthan gum," *Int Pharm.* 2006 Mar. 9; 310(1-2):90-100. Epub 2006 Jan. 18, describe hot-melt extruded compositions of chitosan, specifically hot-melt extruded compositions containing chitosan and xanthan gum.

Examples of water soluble polymers further include polyvinyl alcohol (PVOH) polymers and copolymers. Polyvinyl alcohols are hydrolysis products of polyvinyl acetate or another polyvinyl ester. Polyvinyl alcohols, without modification, tend to be non-thermoplastic, generally having decomposition temperatures below their melting points. However, polyvinyl-alcohol-based compositions may be either externally or internally plasticized so as to exhibit thermoplastic properties. It is known for example to plasticize PVOH by adding such plasticizers as polyethylene glycol, glycerol and neopentyl glycol, thereby giving PVOH compositions thermoplastic properties. Internally plasticized PVOH copolymers include copolymers of vinyl alcohol and (alkyleneoxy)acrylate such as VINEX from Air Products. The physical properties of PVOH, including the strength and water solubility, vary with the degree of crystallinity. Specifically, greater crystallinity typically leads to greater strength and lower water solubility. The degree of crystallinity is dependent, for example, on the degree of hydrolysis and the average molecular weight of the polymer, the amount of plasticizer, the production process (e.g., whether acid or base catalysed). Partially hydrolysed PVOH contains residual acetate groups, which reduce the overall degree of crystallinity of the polymer. Melt processable, pellets of fully hydrolysed PVOH (and plasticizers) are available from Environmental Polymers Group Plc. Annealing a partially or fully hydrolysed PVOH by an annealing process increases the degree of crystallinity of the material and thus reduces its water solubility. For further information regarding polyvinyl alcohol polymers and copolymers see, e.g., U.S. Pat. No. 5,229,124 and "Thermoplastic Poly (Vinyl Alcohol) (PVOH)," Primary author: Nigel Hodgkinson and Michael Taylor, Source: Materials World, vol. 8, pp. 24-25, April 2000, published at Azom.com, as well as the references cited therein.

Thus, the in vivo solubility of a medical device or a portion thereof can be varied by varying the crystallinity of the material, which in turn may be varied by varying the degree of hydrolysis of the polymer, the average molecular weight of the polymer, the amount of additives (e.g., plasticizer, etc.) if any, the production process, the degree of annealing, and so forth.

As previously noted, examples of polymers for forming the devices of the present invention include water soluble polymers and polymers that are soluble in mildly basic (e.g., carboxylated celluloses) or mildly acidic (e.g., chitosan) aqueous solutions. To the extent that the environment into which the device is implanted does not have an ideal pH for dissolution (e.g., because it causes the aqueous soluble polymer to dissolve too slowly or too quickly), the pH may be manipulated by including a pH-adjusting compound (e.g., acid or base) in the device (e.g., the device may contain one or more polymeric regions that comprise one or more polymers and one or more pH-adjusting compounds) or by administering compositions to the subject that change the pH of the in vivo environment where the device is located.

For example, where the device dissolves under mildly alkaline conditions and dissolves too slowly in the implanted environment, a basic compound can be added to the device or a composition may be administered to the subject to make the environment surrounding the device more basic. As another example, where the device dissolves under mildly alkaline conditions and dissolves too quickly in the implanted environment, an acidic compound can be added to the device or a composition may be administered to the subject to make the environment surrounding the device more acidic.

Conversely, where the device dissolves under mildly acidic conditions and dissolves too slowly in the implanted environment, an acidic compound can be added to the device or a composition may be administered to the subject to the subject to make the environment surrounding the device more acidic. As yet another example, where the device dissolves under mildly basic conditions and dissolves too slowly in the implanted environment, a basic compound can be added to the device or a composition may be administered to the subject to make the environment surrounding the device more basic.

Thus, in accordance with one specific embodiment of the invention, a urological device (e.g., a ureteral stent, etc.) is provided which comprises a dissolvable polymer having acidic groups (e.g., oxidized cellulose, etc.) and a basic pH adjusting agent (e.g., an alkali metal hydroxide such as sodium hydroxide, etc.).

In accordance with another specific embodiment of the invention a urological device (e.g., ureteral stent, etc.) is provided which comprises a dissolvable polymer having basic groups (e.g., chitosan, etc.) and an acidic pH adjusting agent (e.g., ascorbic acid, etc.).

In instances where one or more devices are placed within the urinary tract, the pH of the environment surrounding the device can be increased by administering to the subject one or more compositions that alkalinize the subject's urine. Compositions for alkalinizing urine include one or more of the following, among others: carbonic anhydrase inhibitors (e.g., acetazolamide, dichlorphenamide or methazolamide), potassium citrate, sodium citrate, citric acid, sodium bicarbonate, calcium-containing antacids, and magnesium-containing antacids.

On the other hand, the pH of the environment surrounding the device can be decreased by administering to the subject one or more compositions that acidify the subject's urine. Compositions for acidifying urine include one or more of the following, among others: natural products such as cranberry juice, inorganic compounds such as ammonium chloride, and organic compounds such as methenamine, methenamine mandelate, methionine, ascorbic acid, mandelic acids, hippuric acid (found in cranberry juice), and other organic acids.

Thus compositions may be administered to the subject from the time of implantation of a device that is relatively unstable under in vivo conditions to retard dissolution of the medical device in vivo, and such administration may be ceased at a later point in time in order to speed dissolution. Conversely, the medical device may be relatively stable under in vivo conditions, whereas compositions may be administered at the time of implantation or after a certain time period has elapsed in order to speed dissolution.

For example, in accordance with specific embodiment of the invention, a method is provided for increasing the in vivo solubility of a urological medical device that comprises a dissolvable polymer having acidic groups. The method comprises administering to a subject a composition that increases the pH of the subject's urine at a point in time when it is desired to increase the rate of dissolution of the device.

In accordance with another specific embodiment, a method is provided for increasing the in vivo solubility of a urological medical device that comprises a dissolvable polymer having basic groups. The method comprises administering to a subject a composition that decreases the pH of the subject's urine at a point in time when it is desired to increase the rate of dissolution of the device.

In accordance with another specific embodiment, a method is provided for decreasing the in vivo solubility of a urological medical device that comprises a dissolvable polymer having acidic groups. The method comprises administering to a subject a composition that decreases the pH of the subject's urine up until at a point in time when it is desired to increase the rate of dissolution of the device, at which point administration of the composition is discontinued.

In accordance with another specific embodiment, a method is provided for decreasing the in vivo solubility of a urological medical device that comprises a dissolvable polymer having basic groups. The method comprises administering to a subject a composition that increases the pH of the subject's urine up until at a point in time when it is desired to increase the rate of dissolution of the device, at which point administration of the composition is discontinued.

In some embodiments, devices in accordance with the present invention are adapted to release one or more therapeutic agents. For example, the devices of the present invention may contain one or more polymeric regions that comprise one or more polymers and one or more optional therapeutic agents, among other optional additives.

"Therapeutic agents," "drugs," "pharmaceutically active agents," "pharmaceutically active materials," and other related terms may be used interchangeably herein.

Examples of optional therapeutic agents include those which may serve to locally suppress pain and discomfort, for example, an agent selected from steroidal anti-inflammatory agents (e.g., cortisone, etc.), non-steroidal anti-inflammatory agents (e.g., ketorolac, etc.), narcotic analgesic agents (e.g., codeine, morphine, etc.), non-narcotic analgesic agents (e.g., acetaminophen, etc.), anesthetic agents (e.g., novocaine, etc.), antispasmodic agents (e.g., oxybutynin, etc.), or a combination thereof. See U.S. Pat. App. Pub. No. 2003/0224033 to Li et al. for further examples of therapeutic agents.

Where one or more therapeutic agents are present, a wide range of therapeutic agent loadings can be used, with the therapeutically effective amount varying widely based on a number of factors, but being readily determined by those of ordinary skill in the art. Typical loadings range, for example, from 1 wt % or less to 2 wt % to 5 wt % to 10 wt % to 25 wt % or more of the device.

Further optional additives include radio-opacifying agents to facilitate viewing of the medical device during implantation or insertion of the device. A radio-opacifying agent typically functions by scattering x-rays. The areas of the medical device that scatter the x-rays may be detectable on a radiograph. Among radio-opacifying agents useful in the medical device of the present invention are included bismuth salts such as bismuth subcarbonate, bismuth oxychloride, bismuth trioxide, barium sulfate, tungsten, and mixtures thereof, with bismuth salts typically being preferred. Where present, the radio-opacifying agent is typically present in an amount of from about 10% to about 40% (including 10% to 15% to 20% to 25% to 30% to 35% to 40%, with 15-30% being more typical). One skilled in the art can readily determine an appropriate radio-opacifying agent content to achieve the desired visibility.

In some embodiments, the devices of the invention are optionally provided with an agent to facilitate thermoplastic processing (e.g., a plasticizer).

In some embodiments, the devices of the invention are optionally provided with lubricious layers such as water soluble hydrogel layers to facilitate implantation or insertion of the medical device.

Numerous techniques are available for forming wholly or partially biodisintegrable polymeric regions in accordance with the present invention.

For example, where the polymeric regions are formed from one or more components that have thermoplastic characteristics (e.g., a thermoplastic polymer, due to an additive that renders the composition thermoplastic, etc.), a variety of standard thermoplastic processing techniques may be used to form the polymeric regions, including compression molding, injection molding, blow molding, spinning, vacuum forming and calendaring, extrusion into sheets, fibers, rods, tubes and other cross-sectional profiles of various lengths, and combinations of these processes. Using these and other thermoplastic processing techniques, entire devices or portions thereof can be made.

Mixing or compounding the one or more polymer(s) and one or more optional additives (e.g., pH adjusting agents, therapeutic agents, radio-opacifiers, processing aids such as plasticizers, etc.) during processing may be performed using any technique known in the art. For example, a melt may be formed which includes the polymer(s) and one or more optional agents. A common way of doing so is to apply mechanical shear to a mixture. Devices for this purpose include, for example, single screw extruders, twin screw extruders, banbury mixers, high-speed mixers, and ross kettles, among others. Once compounded, the materials can then be processed using any of a variety of thermoplastic processing techniques such as those described above (e.g., extrusion, molding, casting, etc.).

Among the processing conditions that may be controlled during thermoplastic processing are the temperature, applied shear rate, and residence time in the processing device, among others.

Other processing techniques besides thermoplastic processing techniques may also be used to form the polymeric regions in accordance with the present invention, including solvent-based techniques. Using these techniques, a polymeric region can be formed by (a) first providing a solution or dispersion that contains the polymer(s) and any optional agent(s) and (b) subsequently removing the solvent. The solvent that is ultimately selected will contain one or more solvent species, which are generally selected based on their ability to dissolve the polymer(s) (and optional agent(s) as well in many embodiments), in addition to other factors, including drying rate, surface tension, etc. Preferred solvent-based techniques include, but are not limited to, solvent casting techniques, spin coating techniques, web coating techniques, solvent spraying techniques, dipping techniques, techniques involving coating via mechanical suspension including air suspension, ink jet techniques, electrostatic techniques, and combinations of these processes.

In some embodiments of the invention, a polymer containing solution (where solvent-based processing is employed) or a polymer melt (where thermoplastic processing is employed) is applied to a substrate to form a polymeric region. For example, the substrate can correspond to all or a portion of an implantable or insertable medical device to which a polymeric region is applied. The substrate can also be, for example, a template, such as a mold, from which the polymeric region is removed after solidification. In other embodiments, for example, extrusion and co-extrusion techniques, one or more polymeric regions are formed without the aid of a substrate. In a more specific example, an entire stent body may be extruded.

In some embodiments, medical devices in accordance with the invention may contain multiple polymeric layers, for example, a polymeric device body with further layers such as a layer containing an optional radio-opacifying agent, a layer containing an optional therapeutic agent, and/or a layer on an external surface that provides lubricity.

In one specific example, oxidized cellulose is blended with a base (e.g., sodium hydroxide) and a radio-opacifying agent (e.g., bismuth subcarbonate) in a corrosion protected twin screw extruder (e.g., one with a non-corrosive lining on the outside of the screw and on the inside of the barrel to prevent corrosion by the active ingredients in the extruder). The blend is then extruded into stents (after compounding, if desired) of various sizes (e.g., ranging from 5 to 8 Fr). The extruded material is cut to length. If desired, the resulting tube may be machined to provide a tapered tip and/or side ports, and the tube may be annealed to create pigtails like the stent of the FIGURE. A lubricious coating may also be provided as desired.

Various aspects of the invention of the invention relating to the above are enumerated in the following paragraphs:

Aspect 1. An implantable or insertable medical device for supporting a body lumen, the device comprising oxidized cellulose, at least a portion of the device softening or completely dissolving upon implantation or insertion into a subject.

Aspect 2. The implantable or insertable medical device of Aspect 1, further comprising a basic compound.

Aspect 3. The implantable or insertable medical device of Aspect 1, wherein the basic compound is an alkali metal.

Aspect 4. The implantable or insertable medical device of Aspect 1, wherein the device is a urological medical device.

Aspect 5. The implantable or insertable medical device of Aspect 1, wherein the device is a ureteral stent.

Aspect 6. The implantable or insertable medical device of Aspect 1, wherein at least a portion of the medical device comprises a blend of oxidized cellulose and a biostable polymer and wherein that portion of the device softens upon implantation or insertion into the subject.

Aspect 7. The implantable or insertable medical device of Aspect 6, wherein the biostable polymer is an ethylene-vinyl acetate copolymer.

Aspect 8. The implantable or insertable medical device of Aspect 1, wherein the device completely dissolves upon implantation or insertion into a subject.

Aspect 9. The implantable or insertable medical device of Aspect 1, wherein a first portion of the device completely dissolves upon implantation or insertion into a subject and a second portion does not completely dissolve.

Aspect 10. The implantable or insertable medical device of Aspect 9, wherein the device is a ureteral stent having a proximal end and a distal end, and wherein the proximal end completely dissolves and the distal end does not.

Aspect 11. A ureteral stent comprising a polymeric region which comprises a biodisintegrable polymer blended with a biostable polymer, wherein upon placement in a subject, at least a portion of the biodisintegrable polymer is removed from the device by urine being voided by the subject thereby softening the polymeric region.

Aspect 12. The ureteral stent of Aspect 11, wherein the biodisintegrable polymer is a water soluble polymer.

Aspect 13. The ureteral stent of Aspect 11, wherein the polymeric region comprises oxidized cellulose blended with a ethylene-vinyl acetate copolymer.

Aspect 14. The ureteral stent of Aspect 11, wherein the region corresponds to the proximal end of the stent.

Aspect 15. The ureteral stent of Aspect 11, wherein the region corresponds to the entire stent.

Aspect 16. A ureteral stent having a proximal end and a distal end, wherein the proximal end of the stent comprises a biodisintegrable polymer and completely biodisintegrates upon placement in a subject, wherein the distal end of the stent comprises a biostable polymer, a biodisintegrable polymer, or both, and wherein the distal end of the stent remains intact in vivo, partially biodisintegrates in vivo, or completely biodisintegrates in vivo at a slower rate than the rate at which the proximal end dissolves.

Aspect 17. The ureteral stent of Aspect 16, wherein the biodisintegrable polymer is a water soluble polymer.

Aspect 18. The ureteral stent of Aspect 17, wherein the water soluble polymer is oxidized cellulose.

Aspect 19 The ureteral stent of Aspect 16, the distal end of the stent comprises an ethylene-vinyl acetate copolymer and remains intact in vivo.

Aspect 20. A ureteral stent comprising (a) a dissolvable polymer comprising acidic or basic groups and (b) a pH modifying agent, wherein the pH modifying agent is a base where the polymer comprises acidic groups and wherein the pH modifying agent is an acid where the polymer comprises basic groups.

Aspect 21. The ureteral stent of Aspect 20, wherein the polymer comprises carboxyl groups.

Aspect 22. The ureteral stent of Aspect 20, wherein the base is an alkali metal hydroxide.

Aspect 23. The ureteral stent of Aspect 20, wherein the polymer comprises amino groups.

Aspect 24. The ureteral stent of Aspect 20, wherein the acid is ascorbic acid.

Aspect 25. A method comprising administering to a subject a composition that alters the pH of the subject's urine, the subject having inserted or implanted therein a urological medical device that comprises a dissolvable polymer, wherein the composition either slows or accelerates the dissolution of the dissolvable polymer.

Aspect 26. The method of Aspect 25, wherein the dissolvable polymer comprises acidic groups and wherein the composition increases the pH thereby accelerating the dissolution of the dissolvable polymer.

Aspect 27. The method of Aspect 25, wherein the dissolvable polymer comprises acidic groups and wherein the composition decreases the pH thereby slowing the dissolution of the dissolvable polymer.

Aspect 28. The method of Aspect 25, wherein the dissolvable polymer comprises basic groups and wherein the composition decreases the pH thereby accelerating the dissolution of the dissolvable polymer.

Aspect 29. The method of Aspect 25, wherein the dissolvable polymer comprises basic groups and wherein the composition increases the pH thereby slowing the dissolution of the dissolvable polymer.

Aspect 30. The method of Aspect 25, wherein the urological medical device is a ureteral stent.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method of treating a subject, comprising: administering to the subject a composition that alters the pH of the subject's urine, said subject having inserted or implanted therein a urological medical device that comprises a first polymeric portion comprising a dissolvable polymer and a second polymeric portion comprising a non-dissolvable polymer, wherein the composition accelerates the dissolution of said dissolvable polymer.

2. The method of claim 1, wherein said dissolvable polymer comprises acidic groups and wherein the composition increases the pH thereby accelerating the dissolution of said dissolvable polymer.

3. The method of claim 1, wherein said dissolvable polymer comprises acidic groups and wherein the composition decreases the pH thereby slowing the dissolution of said dissolvable polymer.

4. The method of claim 1, wherein said dissolvable polymer comprises basic groups and wherein the composition decreases the pH thereby accelerating the dissolution of said dissolvable polymer.

5. The method of claim 1, wherein said dissolvable polymer comprises basic groups and wherein the composition increases the pH thereby slowing the dissolution of said dissolvable polymer.

6. The method of claim 1, wherein said urological medical device is a ureteral stent.

7. The method of claim 1, wherein the first polymeric portion of the urological medical device is disposed within a bladder of the subject.

8. The method of claim 1, wherein the second polymeric portion of the urological medical device is disposed within a ureter or kidney of the subject.

9. The method of claim 1, wherein the first polymeric portion completely dissolves following administration of said composition.

10. The method of claim 1, wherein the first polymeric portion partially dissolves following administration of said composition.

11. A method of treating a subject, comprising: administering to the subject a composition that alters the pH of the subject's urine, said subject having inserted or implanted therein a urological medical device that comprises a first polymeric portion comprising a dissolvable polymer and a second polymeric portion comprising a partially dissolvable polymer, wherein the composition accelerates the dissolution of said dissolvable and partially dissolvable polymers.

12. The method of claim 11, wherein the dissolvable polymer of the first polymeric portion dissolves more slowly than the partially dissolvable polymer of the second polymeric portion.

13. The method of claim 11, wherein said dissolvable and partially dissolvable polymers comprise acidic groups and wherein the composition increases the pH thereby accelerating the dissolution of said dissolvable and partially dissolvable polymers.

14. The method of claim 11, wherein said urological medical device is a ureteral stent.

15. The method of claim 11, wherein the first polymeric portion of the urological medical device is disposed within a bladder of the subject.

16. The method of claim 11, wherein the second polymeric portion of the urological medical device is disposed within a ureter or kidney of the subject.

17. The method of claim 11, wherein the first polymeric portion completely dissolves following administration of said composition.

18. The method of claim 11, wherein the first polymeric portion partially dissolves following administration of said composition.

* * * * *